United States Patent
Myhr (10) Patent No.: US 7,220,258 B2
(45) Date of Patent: May 22, 2007

(54) THERAPEUTIC PROBE, METHOD AND SYSTEM

(75) Inventor: Gunnar Myhr, Jar (NO)

(73) Assignee: Cancercure AS (NO)

( * ) Notice: Subject to any disclaimer, the term of this patent is extended or adjusted under 35 U.S.C. 154(b) by 0 days.

(21) Appl. No.: 10/610,531

(22) Filed: Jul. 2, 2003

(65) Prior Publication Data
US 2004/0187876 A1  Sep. 30, 2004

(51) Int. Cl.
*A61B 18/18* (2006.01)

(52) U.S. Cl. ............................ 606/28; 600/439; 606/46

(58) Field of Classification Search ............... 601/2–3; 606/27–50; 600/439
See application file for complete search history.

(56) References Cited

U.S. PATENT DOCUMENTS

| | | | |
|---|---|---|---|
| 4,315,514 A | 2/1982 | Drewes | |
| 4,561,446 A | 12/1985 | Hetz | |
| 4,869,246 A * | 9/1989 | Adair | 606/7 |
| 5,176,142 A | 1/1993 | Mason | |
| 5,320,104 A | 6/1994 | Fearnside | |
| 5,471,988 A * | 12/1995 | Fujio et al. | 600/439 |
| 5,588,432 A * | 12/1996 | Crowley | 600/439 |
| 5,895,356 A * | 4/1999 | Andrus et al. | 600/439 |
| 5,967,968 A | 10/1999 | Nishioka | |
| 5,984,882 A * | 11/1999 | Rosenschein et al. | 601/2 |
| 6,210,356 B1 * | 4/2001 | Anderson et al. | 604/22 |
| 6,308,714 B1 * | 10/2001 | Peterson et al. | 128/898 |
| 6,315,712 B1 | 11/2001 | Rovegno | |
| 6,425,867 B1 | 7/2002 | Vaezy | |
| 6,514,249 B1 * | 2/2003 | Maguire et al. | 606/41 |
| 6,527,759 B1 | 3/2003 | Tachibana | |
| 6,821,274 B2 * | 11/2004 | McHale et al. | 606/41 |
| 2001/0002251 A1 | 5/2001 | Woodburn | |
| 2001/0007666 A1 | 7/2001 | Hoffman | |

FOREIGN PATENT DOCUMENTS

WO  WO 02/15976  2/2002

* cited by examiner

*Primary Examiner*—Michael Peffley
(74) *Attorney, Agent, or Firm*—Bacon & Thomas PLLC (57) ABSTRACT

The invention relates to an acoustic probe for treating cancerous tissue, for introduction into a natural or surgically created cavity in the patient, in close proximity to a tissue area which includes cancerous cells. The probe includes an acoustic transmitter arranged for transmitting an acoustic signal having characteristics which causes damage of said cancerous cells and means for administering chemotherapeutic substances. The invention further relates to a corresponding method and a system for treating cancerous tissue. The use of the invention may be combined with the use of encapsulated cytostatica within micelles or therapeutic molecules.

41 Claims, 8 Drawing Sheets

THERAPEUTIC PROBE, METHOD AND SYSTEM

FIELD OF THE INVENTION

The present invention relates generally to the treatment of cancer.

More specifically, the invention relates to a probe, a method and a system for treating cancerous tissue, wherein an acoustic probe is introduced into the body of a human or animal, hereinafter denoted a patient. The acoustics may interact with encapsulated cytostatica within micelles.

The present invention is a further development of the applicant's prior International Patent Application PCT/NO01/00349 "Apparatus for selective cell and virus destruction within a living organism", published 28 Feb., 2002 (WO 02/15976), which is hereby incorporated by reference.

BACKGROUND OF THE INVENTION

Traditional treatment of cancer has been combinations of medicine (surgery), radiation and biochemical processes. In this context a major problem has been to differentiate between cancer cells and normal cells, that cancer cells have developed resistance against chemotherapy, in combination with critical location of tumours and/or metastases. An approach that has previously not been systematically used in the treatment of cancer is to utilise the differences in biophysical properties to selectively attack and destroy cancer cells, specifically by:

External mechanical stress and strain
Inducing apoptosis and/or necrosis
Traditional methods of treatment like chemotherapy/antioxidants in synergy with the use of acoustics
Combinations of the above stated procedures Related to externally induced mechanical stress, any body or systems of bodies, both physical and biological, has or can oscillate at various natural frequencies. Based on the significant differences in internal and external structure between cancer and normal cells, there are qualified reasons to believe that the mechanical resonance frequencies of normal cells and the equivalent for cancer cells are quite different.

A methodology for the application of resonance frequencies was first introduced in U.S. Pat. No. 4,315,514.

Apoptosis is a mechanism by which cells are programmed to die under a wide range of physiological, biochemical and developmental stimuli. From the perspective of cancer, apoptosis is both a mechanism which suppresses tumour genesis and is a predominant pathway in antineoplastic therapy. Many cancer cells circumvent the normal apoptotic mechanisms to prevent their self-destruction because of the many mutations they harbour. Thus, disarming apoptosis and other surveillance mechanisms is of fundamental significance in allowing the development of the malignant and metastatic phenotype of a cancer cell.

U.S. Pat. No. 5,984,882 describes a methodology for the treatment of cancer by inducing apoptosis with the use of ultrasonic energy.

The combination of ultrasound and chemotherapy are discussed in U.S. App. No. 20010007666 and U.S. App. Ser. No. 20010002251, which provide methodologies for the combination of various substances with ultrasonic sound for selective cell destruction.

Also, U.S. Pat. No. 6,308,714 describes a method for enhancing the action of anti-cancer agents with the combination of ultrasound.

Scientific evidence supporting the hypothesis of selective cell destruction by the combination of chemicals and ultrasound are provided in the literature. Wörle, Steinbach, Hofstädter (1994) [Cancer January;69(1)] studied the combined effects of high-energy shock waves and cytostatic drugs or cytokines on human bladder cancer cells. Maruyama et. al. (1999) [Anticancer Res May–June;19 (3A)] studied the application of high energy shock waves to cancer treatment in combination with cisplatin and ATX-70 both in vitro and in vivo. Kato et. al. (2000) [Jpn J Cancer Res October;91(10)] investigated the mechanism of antitumour effect by the combination of bleomycin and shock waves. In this study they evaluated the synergistic effects on cancer cell proliferation and apoptosis in solid tumours.

The most compelling evidence of the effects of anticancer agents in combination with low-frequency ultrasound is provided by Nelson et. al. (2002) [Cancer Res December 15;62(24):7280–3]. They developed a novel drug delivery system that released drug from stabilized micelles upon application of low-frequency ultrasound and demonstrated efficacy using doxorubicin (Dox) to treat tumours in vivo. Forty-two BDIX rats were inoculated in each hind leg with a DHD/K12/TRb tumour cell line. Dox was encapsulated within stabilized Pluronic micelles and administered weekly i.v. to the rats starting 6 weeks after the tumour inoculations. One of the two tumours was exposed to low-frequency ultrasound for 1 h. Dox concentrations of 1.33, 2.67, and 8 mg/kg and ultrasound frequencies of 20 and 70 kHz were used for treatment. Application of low-frequency ultrasound (both 20 and 70 kHz) significantly reduced the tumor size when compared with noninsonated controls (P=0.0062) in the other leg for rats receiving encapsulated Dox. Significant tumour reduction was also noted for those rats receiving ultrasound and encapsulated Dox at 2.67 mg/kg (P=0.017) and rats receiving Dox and ultrasound at 70 kHz (P=0.029). They postulate that ultrasound releases the Dox from the micelles as they enter the insonated volume, and ultrasound could also assist the drug and/or carriers to extravasate and enter the tumour cells.

There may be a desire to bypass certain tissue or omitting the exposuring of specific organs, to locate or gain excess to, and/or target specific organs or cancerous tissue, or to treat tumours or metastatic tissue within or adjacent to body (air filled) cavities, with or without locally administered encapsulated cytostatica. In this respect a need for an endoscopic device for the (partial) treatment of cancer or cancerous tissue or organs with the use of acoustics is apparent.

Experiments

To provide evidence of selective cell destruction by acoustics, research were conducted with the use of balb/c nude mice with WiDr tumours transplanted on the right leg.

The aim of the experiments was to establish relevant frequencies where selective energy absorption occurred in malign tissue, and to conduct treatment at such frequencies on malign tumours.

Figure 1:
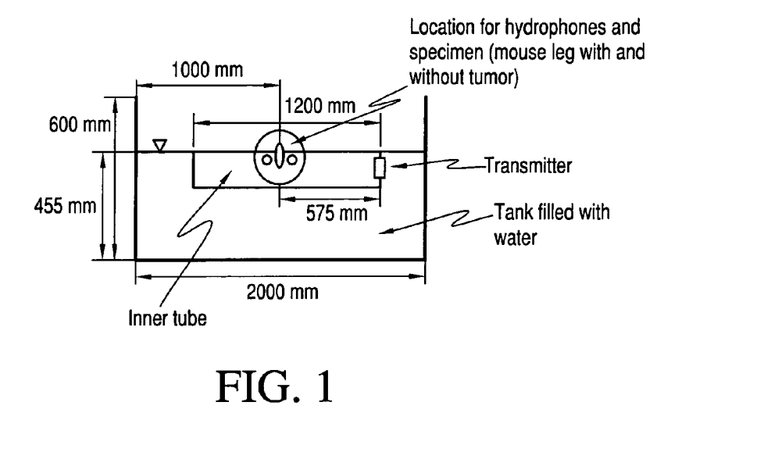
FIG. 1 illustrates equipment used in an experimental arrangement FIG. 2 further illustrates the experimental arrangement
Figure 2:
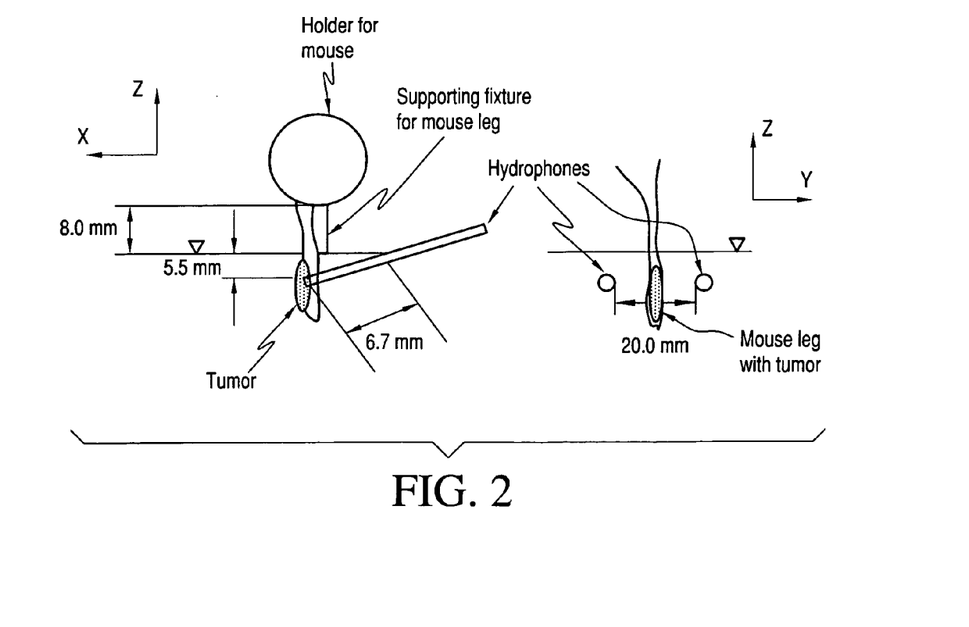
Figure 3A:
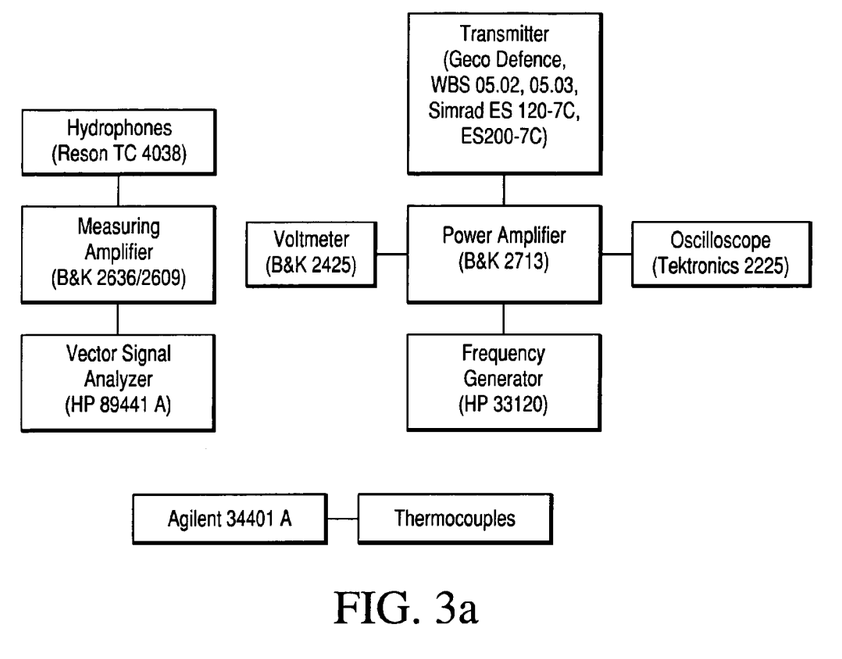
FIG. 3a is a schematic block diagram for equipment used in a first experimental arrangement.

With the use of an experimental set up as described in FIGS. 1, 2 and 3a, mice were placed in a cylindrical holder with one leg inserted into non-degassed water. Submerged hydrophones were placed on each side of the leg, with an acoustic transmitter located at one end of the tank.

To establish relevant frequencies where selective energy (pressure) absorption could be apparent, a spectroscopy study on five mice over a relatively wide frequency range was conducted. One mouse drowned during the experiments; causing the experiments to be finalized with four animals. The frequency range for the spectroscopy phase was from 9 kHz to 206 kHz, stepwise recording, based on the following frequency intervals:

TABLE 1

Interval for stepwise recording.

| Range (kHz) | Δf |
|---|---|
| 8–25 | 1 |
| 27–51 | 2 |
| 54–75 | 3 |
| 79–103 | 4 |
| 108–128 | 5 |
| 134–164 | 6 |
| 171–206 | 7 |

Relevant data for the mice which were subjected to spectroscopy are provided in table 2. All numbers are in mm.

TABLE 2

Relevant data for the mice subjected to spectroscopy.

| l | b | h | d | D1 | D2 | D3 |
|---|---|---|---|---|---|---|
| 10.2 | 4.9 | 5.4 | 2.6 | 19.2 | 4.6 | 21.4 |
| 9.0 | 5.8 | 7.2 | 2.5 | 16.2 | 4.9 | 24.2 |
| 9.9 | 7.6 | 7.5 | 2.6 | 25.0 | 4.1 | 25.5 |
| 10.6 | 6.1 | 5.3 | 2.8 | 23.6 | 5.0 | 22.9 | l = length of tumour
b = width of tumour
h = thickness of tumour including leg
d = diameter (thickness) of leg
D1 = Distance from holder to lower end of tumour
D2 = Distance from lower end of tumour to toe tip
D3 = Distance from holder to toe tip (healthy leg)

With continuous emission, voltage set at 70 V, exposure time 15 seconds at each frequency and ambient water temperature approx. 28.5 degrees C., Δp were measured over the leg with and without tumour (right leg vs. left leg) as a function of frequency.

As discussed in the chapter to follow concerning attenuation, the impedance of biological matter is inversely related to the water content of the material in question. Based on this analysis, the pressure drop for the healthy legs were expected to be larger than for legs with tumours. The experimental data were in accordance with this hypothesis.

Due to individual developments of the various tumours, their location on the legs varied. This again caused the proportion of the total leg which were submerged to vary for the different mice. To compensate for these effects, the pressure decrease over the legs were related to the length of the submerged leg.

Figure 4:
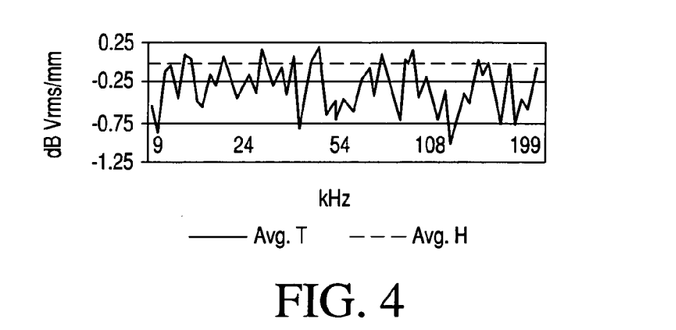
FIG. 4 is a pressure difference graph illustrating experimental results.

FIG. 4 provides a graph of Δp divided by length of the submerged leg for the legs with tumours minus the equivalent for healthy legs.

Data showed significant selective (pressure) absorption at 27, 45, 72 and 91, all kHz, and to some extent 14 kHz.

Based on the results from the analysis of the spectroscopy data, actual treatment were conducted by the use of the following frequencies; 27 (group of 6 mice), 45 (group of 5 mice) and 91 (group of 6 mice), all kHz. Emission was continuous, voltage set at 80 V, exposure time 10 minutes, ambient water temperature approx. 28.5 degrees C.

An additional experiment on a group of 5 animals, exposed at 45 kHz for 10 minutes was conducted, but with pulsed emission. The pulse length was 2.22 ms, repetition rate 100 Hz, amplitude 20 V, voltage (peak to peak) 200 V. After the experiments, length (l), width (w) and height (h) of the tumours were measured every second day (one period), where the time of treatment is defined as period 0.

The volume of the tumours were calculated by the formula (l×w×h)π/6 (ellipsoidal approximation).

Due to the aggressive nature of the WiDr tumours, we had to start to eliminate mice after three periods.

TABLE 3a

Variance analysis versus control-experiments one.

| Group | Est. α | p | Est. β | p |
|---|---|---|---|---|
| 1 | 44.00 | 0.2287 | −34.79 | <0.0001 |
| 2 | −3.18 | 0.9159 | −6.44 | 0.3446 |
| 3 | 43.79 | 0.2648 | −18.79 | 0.0592 |
| 6 | 36.28 | 0.2908 | −29.35 | 0.0002 |

TABLE 3b

Actual model for the various treatment categories-experiments one.

| Group | Est. α | p | Est. β | p |
|---|---|---|---|---|
| 1 | 93.49 | 0.0038 | 20.44 | 0.0027 |
| 2 | 46.31 | 0.0087 | 48.79 | <0.0001 |
| 3 | 93.29 | 0.0074 | 36.44 | 0.0041 |
| 6 | 85.77 | 0.0036 | 25.88 | 0.0034 |
| Control | 49.49 | 0.1754 | 55.24 | 0.0005 |

Figure 5A:
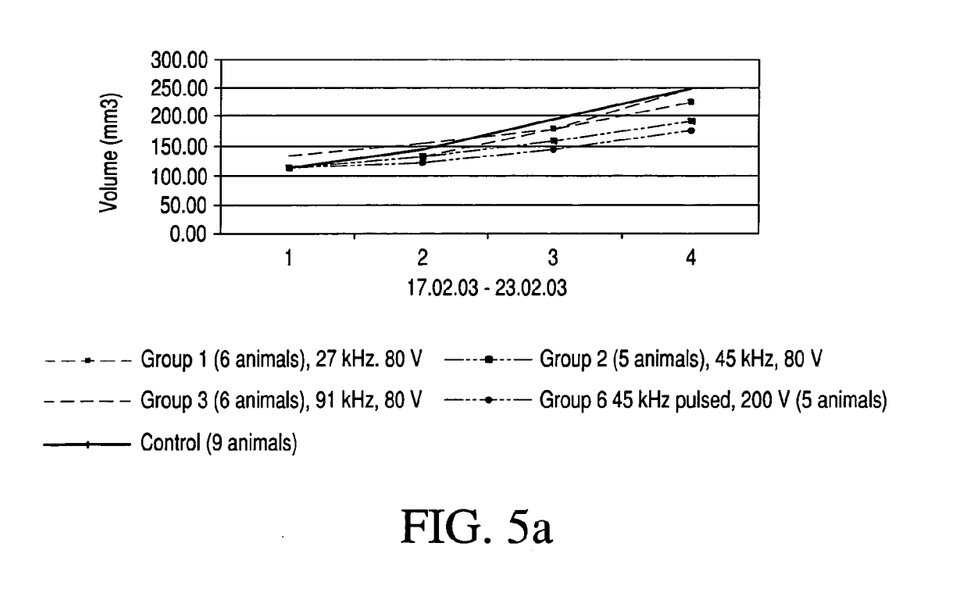
FIG. 5a is a tumour development graph illustrating first experimental results.

Based on the data in FIG. 5a, a variance analysis was performed. The various groups were firstly analysed versus the control group, and secondly against itself. The data were analysed based on the equation:

$$(\text{Volume})_{group} = \alpha + \beta(\text{treatment})_{group} * (\text{time}) \quad (1)$$

As seen from table 3a, groups 1 (27 kHz) and 6 (45 kHz pulsed) provided significance against the control group.

Table 3b represents actual fits for the various groups.

Thermocouples were applied into the tumours for both spectroscopy and treatment, but no significant temperature increase (ΔT<0.1° C.) was apparent.

Due to significant wavelengths at these frequencies (5.6 cm at 27 kHz and 1.6 cm at 91 kHz), the problem of standing waves, and distance from the source (emitter) to the tumour is of great significance.

Total acoustic energy which was emitted was in the range of 3 W. Intensity at the source was 0.01 W/cm², based on an area of the sphere of 277.6 cm².

Figure 3B:
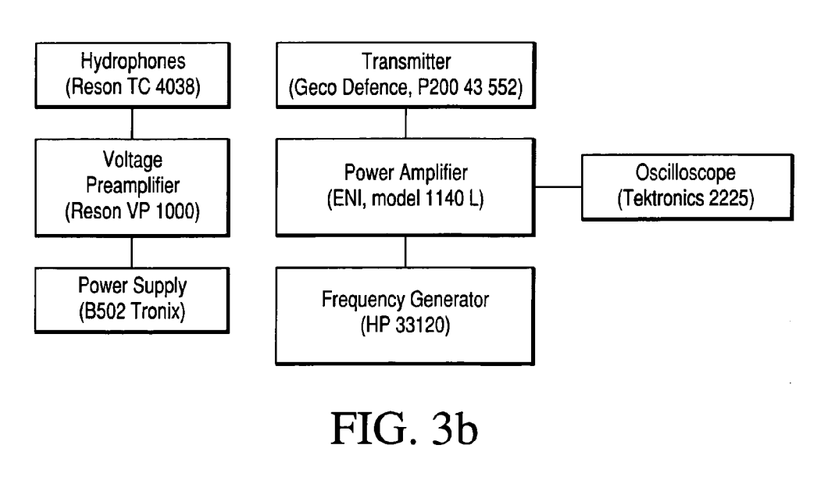
FIG. 3b is a schematic block diagram for equipment used in a second experimental arrangement.

A second set of experiments were conducted with a slightly different set up, ref. FIG. 3b, with same type of mice, cancer line and tumour location.

The various treatment groups were:

Group 1

9 animals, f=27 kHz, applied voltage to the power amplifier=350 V peak to peak, I=2.2 A, exposure time=15 min.

Group 2

9 animals, f=91–95 kHz, Δf=1 kHz, applied voltage to the power amplifier=350 V peak to peak, I=1.1–1.4 A, exposure time=3 min. at each frequency.

Group 3

9 animals, f=31–35 kHz, Δf=1 kHz, applied voltage to the power amplifier=300 V peak to peak, I=2.6 A, exposure time=3 min. at each frequency.

Group 5

9 animals, f=13–17 kHz, Δf=1 kHz, applied voltage to the power amplifier=300 V peak to peak, I=0.5 A, exposure time=3 min. at each frequency.

Control, 16 animals.

Figure 5B:
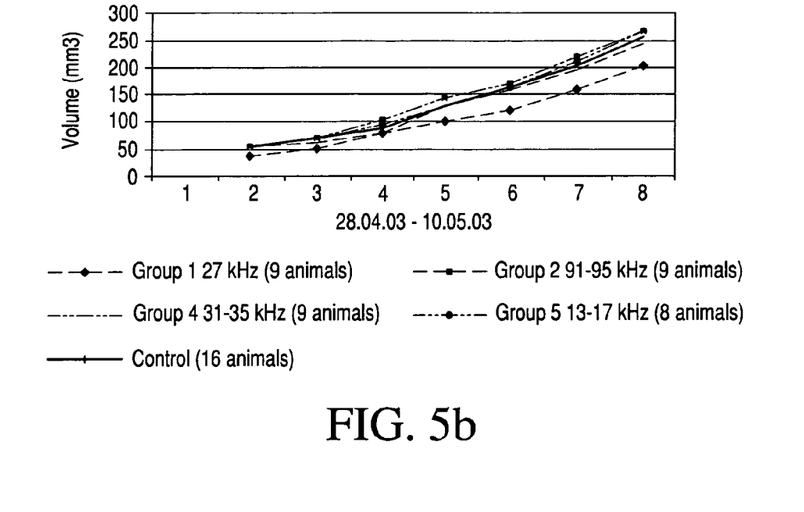
FIG. 5b is a tumour development graph illustrating second experimental results.

Equivalent to experiment one, and based on the data in FIG. 5b, a variance analysis was performed. The various groups were firstly analysed versus the control group, and secondly against itself. The data were analysed based on the equation:

$$(Volume)_{group} = \alpha + \beta 1 (treatment)_{group} * (time) + \beta 2 (treatment)_{group} * (time)^2 \quad (2)$$

As seen from table 3c, group 1 (27 kHz) was the only group that provided significance against the control group.

Table 3d represents actual fits for the various groups.

TABLE 3c

Variance analysis versus control-experiments two.

| Group | Est. α | p | Est. β1 | p | Est. β2 | p |
|---|---|---|---|---|---|---|
| 1 | −66.39 | 0.0506 | 28.47 | 0.0114 | −4.33 | 0.0008 |
| 2 | −12.20 | 0.7526 | 7.57 | 0.5259 | −0.55 | 0.6772 |
| 3 | −10.42 | 0.7959 | 6.88 | 0.6443 | −1.19 | 0.4784 |
| 5 | −26.13 | 0.6179 | 15.67 | 0.2223 | −2.00 | 0.1431 |

TABLE 3d

Actual model for the various treatment categories-experiments two.

| Group | Est. α | p | Est. β1 | p | Est. β2 | p |
|---|---|---|---|---|---|---|
| 1 | 4.58 | 0.8120 | 15.69 | 0.0415 | 2.45 | 0.0086 |
| 2 | 58.78 | 0.0541 | −5.19 | 0.5496 | 6.23 | <0.0001 |
| 3 | 60.55 | 0.0568 | −5.89 | 0.6370 | 5.58 | 0.0015 |
| 5 | 44.85 | 0.3340 | 2.90 | 0.7661 | 4.78 | 0.0019 |
| Control | 70.98 | 0.0148 | −12.77 | 0.1313 | 6.78 | <0.0001 |

There are problems with acoustic impedance related to air, and subsequently the boundary layers between or within tissue or organs and air. In this respect the issue of tumours, metastases or cancerous tissue related to body cavities, or air within organs has to be addressed.

As mentioned, an answer to these challenges may be acoustic endoscopic procedures, devices and system, with or without the use of chemotherapeutic substances, which may or may not be encapsulated within therapeutic molecules. In the analysis to follow, we set the scene by firstly discussing the topic of attenuation. This is followed by a general discussion related to endoscopy and ultrasonic probes in particular, before new endoscopic techniques, apparatuses, method and system related to cancer treatment, are outlined.

Attenuation

The concept attenuation describes the total reduction in intensity (I) of an acoustic beam which propagates in a defined direction (x) within a medium.

Attenuation has its background in;

Absorption of energy in the medium

Deflection of energy due to reflection, refraction, diffraction and scatter.

Absorption involves the transition of acoustic energy into a different energy form (heat). Reflection, refraction, diffraction and scatter causes the sound to transmit in different directions than the direction of propagation. While absorption is dependent on the state of the medium, deflection is both dependent on geometry and physical properties of the object. Reflection and refraction may occur at the boundary layer between regions with different impedance. In this context are the particle pressure, p, the particle velocity, v, related by the expression;

$$p = \rho c v \quad (3)$$

where $\rho$=density of the matter c=speed of sound in the material

The expression $p/v = Z = \rho c$, is called the characteristic impedance.

Diffraction may occur by a barrier or obstruction in the direction of propagation. Scatter is due to the structure of the material.

For a sound wave which propagates in x-direction in a specific type of tissue, the incremental intensity loss δI will be proportional with the intensity, I, and δx.

Subsequently we obtain;

$$I(x) = I_0 e^{-\mu(f)x} \quad (4)$$

where

I(x)=intensity at tissue depth x $I_0$=initial intensity

μ(f)=intensity absorption coefficient

Assuming that $Attenuation_{absorption} >> Attenuation_{deflection}$ such that any deflection effects are neglected in the calculations to follow.

Attenuation is measured in neper (Np) or decibel (dB). It can be shown that 1 Np=8.886 dB.

μ (f) has subsequently the notation Np per unit of length (cm).

μ(f) relates to frequency by the expression;

$$\mu(f) = A(f/f_1)^m \quad (5)$$

Combining equation (4) with the expression $\lambda = c/f_1$, one obtains the absorption coefficient per unit of wave length;

$$\mu\lambda = A(cf^{m-1})/f_1^m \quad (6)$$

For soft tissue μ varies with frequency raised in the power of one, while for e.g. water it varies with the power of two.

By assuming m=1, equation (5) indicates that μλ can be independent of frequency.

Figure 6:
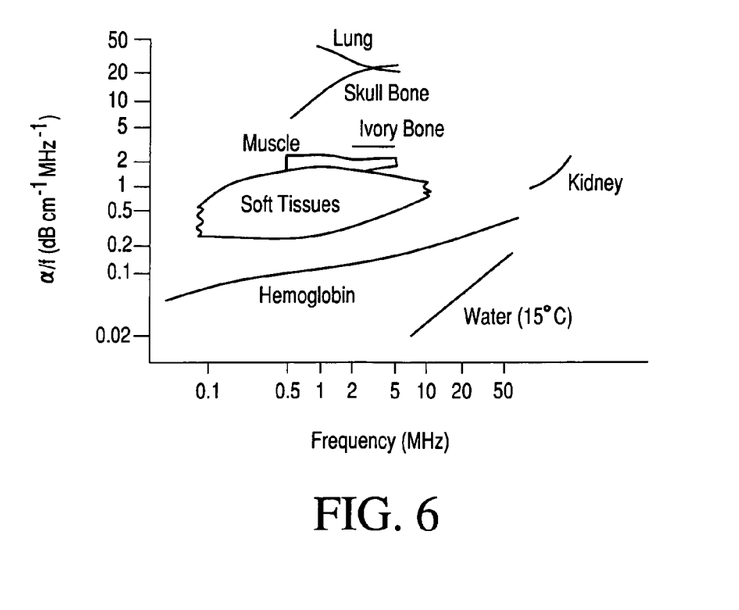
FIG. 6 is a graph illustrating attenuation variation for various biological material.

FIG. 6 shows absorption, defined as α/f, where α=μ/2, as a function of frequency for various types of biological matter. Absorption for the different organs is to a large degree independent of frequency over large frequency ranges. For water it is apparent that attenuation effects first occur at significantly high frequencies (+5 MHz), and that a strong functional relationship to actual frequency is apparent at these frequencies.

Based on table (4) and equation (4) one can calculate the intensity absorption coefficients for various types of matter or tissue.

By studying table 4, it is clear that the absorption coefficient reduces with increasing water content of the tissue.

TABLE 4

Parameters to calculate intensity absorption coefficients for variuos types of tissue/matter. Basis for
$f_1 = 1$ MHz.
Source: Duck (1990) ["Physical Properties of Tissue", Academic Press, San Diego], Vlieger et. al. (1977) ["Handbook of Clinical Ultrasound", John Wiley & Sons, New York].

| Type of tissue/matter | A(Np/cm) | m |
|---|---|---|
| Cranium | 2.3 | 1.7 |
| Muscle, human along the fibers | 0.66 | 1.0 |
| Muscle, human normal to the fibers | 0.26 | 1.0 |
| Fat, human, stomach | 0.14–1.2 | (0.4)–1.4 |
| Blood | 0.046 | 1.3 |
| Water | 0.00046 | 2.0 |
| Air (STP) | 2.3 | 2.0 |

In table 5 we have calculated the intensity loss at tissue debts of 0.5 cm and 0.25 cm for muscle mass with wave front both along and normal to the fibers at 100 kHz, 50 kHz, 25 kHz and 10 kHz.

As seen from the table, an absorption rate equivalent to 3.3% is evident at 100 kHz, tissue debt of 0.5 cm and wave front along the fibers. This is reduced to 0.1% at 10 kHz, tissue debt of 0.25 cm and wave front normal to the muscle fibers.

TABLE 5

Intensity loss at tissue debts of 0.5 cm and 0.25 cm for human muscle tissue with wave front along and normal to the muscle fibers.

|  | 100 kHz | 50 kHz | 25 kHz | 10 kHz |
|---|---|---|---|---|
| $I(0.5\ cm)/I_0$ | | | | |
| Along the fibers | 0.967 | 0.983 | 0.991 | 0.996 |
| Normal to the fibers | 0.987 | 0.993 | 0.996 | 0.998 |
| $I(0.25\ cm)/I_0$ | | | | |
| Along the fibers | 0.983 | 0.991 | 0.995 | 0.998 |
| Normal to the fibers | 0.993 | 0.996 | 0.998 | 0.999 |

The above stated theoretical analysis, which indicates low intensity losses due to absorption for the frequencies in question, supports the empirical findings of the lack of temperature increase, even though there are additional complicating factors like conductivity to ambient water, heat transfer due to blood supply etc.

Also, the reversed effect may be apparent, that the acoustic energy may be trapped within a body, due to its insulation by air.

Endoscopy in General

Endoscopy is a well established medical procedure for both diagnosis and treatment within body cavities. The procedure uses a flexible lighted tube with a lens or video camera on the end, with the additional possibility of an instrument channel for the use of tools to cut, burn, apply various needles, and the like. If a camera is used it is connected to a display unit for viewing.

For upper endoscopy the tube is passed through the mouth to view the esophagus, stomach and the first part of the bowel.

A colonoscope is a type of endoscope that is inserted through the anus, the rectum and into the colon. Colonoscopy allows the therapist to see the lining of the entire colon.

The combination of the ultrasound probe and an endoscope have led to the development of echoendoscopes. Endoscopic ultrasound combines an ultrasound processor on the tip of an endoscope, allowing for improved ultrasound imaging of the gastrointestinal tract and the abdominal organs adjacent to it. These instruments allow for the examination of both the lining of the digestive tract with the endoscope, in addition to the wall of the tract and its surrounding structures such as the liver, pancreas, bile ducts, and lymph nodes.

It is also possible to study the flow of blood in vessels by Doppler ultrasound. Also, to pass a small needle down the endoscope and direct it, under ultrasound guidance, into structures within or adjacent to the digestive tract, such as lymph nodes or suspicious tissue, can be performed. In this way, tissue can be aspirated for analysis by a pathologist. This technique is known as fine needle aspiration (FNA).

Small flexible catheters have been developed that can be passed through a regular endoscope. They are referred to as "miniprobes" or "catheter probes". They provide high frequency ultrasound images, often in the 12–30 MHz range, while standard diagnostic ultrasound are performed in the 3 MHz–8 MHz range, which allow for very detailed images of e.g. the wall of the gastrointestinal tract.

Echoendoscope procedures can provide a variety of information. It is primarily used to detect suspected cancers or to evaluate how far a previously diagnosed cancer has spread in order to determine the appropriate therapy. Echoendoscopy is also used to stage cancers of the esophagus, stomach, pancreas, and rectum. Spread to adjacent lymph nodes and blood vessels can be determined by the imaging and fine-needle aspiration capabilities of echoendoscope. Echoeindoscope gives partial, but incomplete, information regarding the spread of these tumours to adjacent organs due to its limited depth of penetration. However, imaging enhancements may allow for greater evaluation of adjacent organs.

More recent applications have been to evaluate patients with fecal incontinence. stage lung cancers, and to evaluate for clots in the vessels of the abdomen with the use of Doppler.

If a fluid collection is seen, it can be suctioned through the scope and the fluid sent for analysis. Occasionally, if there is a cyst that needs drainage, a cyst-gastrostomy or a cyst-duodenostomy may be performed, by placing a stent through the stomach or small bowel into the cyst.

For patients with pancreatic cancer and severe pain, a celiac-plexus blockade can be performed in which medications will be injected into the nerves responsible for transmitting this pain. This can lessen the pain in these patients for a period of up to several months.

Further Prior Art

Ultrasonic probes which can be introduced into a body are well known. E.g. U.S. Pat. No. 4,561,446 describes a probe tube which an ultrasonic array is disposed. The primary aim of the device is the employment for bladder endoscopy of male patients. The system comprises an optical insert and an ultrasonic array which are disposed in two layers radially offset and also offset relative to one another in the longitudinal direction of the tube.

Also, U.S. Pat. No. 5,176,142 describes an endoscopic ultrasound probe which has a rotatable transducer array for obtaining two-dimensional cross-sectional images of a subject along a variety of scan planes. The probe also has a take-up mechanism comprising a flexible cable assembly which is electrically connected to an array for remote ultrasound imaging system. U.S. Pat. No. 5,320,104 is quite similar to U.S. Pat. No. 5,176,142, but it represents an endoscopic ultrasound probe specifically for use in transesophageal echo cardiography comprising a rotatable ultrasound transducer array for obtaining two-dimensional cross-sectional images. Among other related technologies. U.S. Pat. No. 5,967,968 describes an endoscopic imaging system for viewing an object within a patient's body cavity including an endoscope for viewing an image of the object. The endoscope comprising a distal end, an instrument channel, and a probe to determine the size of an object. U.S. Pat. No. 6,315,712 comprises a video endoscopic probe which has a distal terminal, utilizing an objective, a colour CCD (charge-couple device) sensor, and an electrical interface microcircuit. The probe utilizes a continuous bundle of optical fibers which is coupled to a light source.

Objects and Summary of the Invention

An object of the present invention is to provide a probe, a method and a system for treating cancer in a patient, preferably a human, alternatively an animal patient.

A further object of the present invention is to provide a probe, a method and a system for destroying tumours or cancerous cells and tissue, with or without the combination of encapsulated cytostatica.

A further object of the present invention is to provide a probe, a method and a system for treating cancerous tissue, which is less detrimental to the patient than prior art methods.

Further objects of the present invention will be apparent from the above background of the invention in conjunction with the following detailed description of the invention.

The objects stated above, as well as further advantages and favorable results, are achieved by means of a probe, a method and a system as set forth in the appended set of claims.

BRIEF LIST OF DRAWINGS

The invention will be described in further detail by reference to the figures, wherein.

DETAILED DESCRIPTION OF A PREFERRED EMBODIMENT

FIGS. 1, 2, 3a, 3b, 4, 5a, 5b, and 6 are previously described with reference to the background of the invention.

Figure 7A:
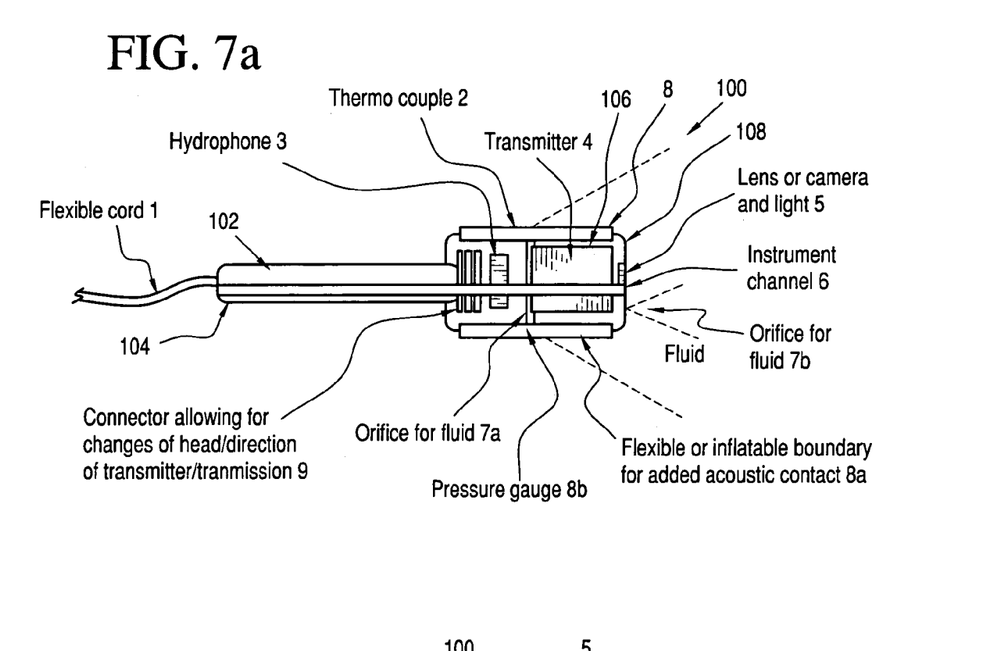
FIG. 7a is a schematic sectional view of a probe according to the invention.
Figure 7B:
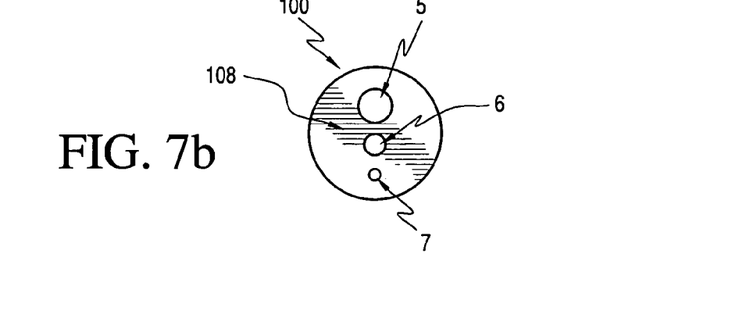
FIG. 7b is a schematic front view of the probe.

FIG. 7a is a schematic sectional view of a probe according to the invention, and FIG. 7b is a schematic front view of the probe, The probe 100 is an acoustic probe for treating cancer or cancerous tissue within a patient. In use, the probe is introduced into a natural or surgically created cavity in the patient, in close proximity to a tissue area which includes cancerous cells. The probe 100 includes an acoustic transmitter 4, arranged for transmitting an acoustic signal having characteristics which causes damage of said cancerous cells.

The probe 100 comprises a substantially cylindrical housing 102 with a proximal portion or shaft 104, and a distal portion or instrument body 106. In the illustrated embodiment, the proximal portion 104 has a less diameter than the distal portion 106. At the distal end of the probe 100, the housing 102 of the probe comprises a front face 108.

A flexible cord 1 is provided at the proximal end 104 of the housing 102. The cord 1 comprises optical, electrical and hydraulic connections to the probe from an external control arrangement and an external fluid supply.

An acoustic transmitter 4 is provided at the distal portion 106 of the probe 100. In the illustrated embodiment, the transmitter is arranged at the front face of the housing, and the transmitter is forward directive.

The probe also comprises an electrical communication connection, included in the flexible cord 1, for supplying the transmitter with an electrical signal from an external control arrangement.

The acoustic signal characteristics may include a natural resonance frequency of said cancerous cells. Alternatively or in addition, the characteristics include an apoptosis frequency of said cancerous cells, or a necrosis frequency of said cancerous cells. The signal may be a continuous signal comprising only one frequency component, or a continuous, composite signal with a spectrum of more than one frequency component, or alternatively a discontinuous signal, changing between various frequencies or frequency spectra during different periods of time.

The signal frequency is preferably in the range of 1 kHz to 1 MHz, and particularly advantageously in the range of 1 kHz to 100 kHz.

The probe further comprises, at the front face, at least one orifice or outlet 7a and/or 7b for supplying a liquid from the probe to the body cavity. The main purpose of these orifices 7a and 7b are to provide an acoustic medium between the probe and the tissue cleansing. The probe further comprises a liquid connection line for supplying the orifice with the liquid from an external liquid supply.

The liquid is preferably distilled (degassed) water. The purpose of the liquid injection is to obtain maximum acoustic conductivity, and the possibility for cleansing. As explained below, the liquid may also act as a medium for driving a locking means, in particular a flexible jacket, between the probe and the body tissue.

In a particular embodiment of the invention, encapsulated or non-encapsulated chemotherapeutical agents (cytostatica) within micelles or therapeutic molecules are supplied to the cancerous tissue by separate means, which may include the supply of such substances through an instrument channel of the probe and/or the system.

The probe further comprises an optical viewing device 5 for providing image data, and an optical or electrical communication connection for transferring the image data to an external control arrangement.

The optical viewing device 5 is provided at the front face 108. Preferably, the optical viewing device comprises an electronic camera and a light source. The purpose of the viewing device is to provide images of internal organs, body cavities or tissue.

The electronic camera is a miniaturized digital camera based on a high sensitivity colour CCD sensor. A video signal connection line is provided in the cord for connecting the camera to the external control arrangement, which includes a video card including a DSP (digital signal processor) image analysis processor, a microcontroller for modifying the DSP functions, and an on screen display for direct viewing on a monitor.

The light source is preferably the end of a fiber optic cable fed through the flexible cord, transferring light from a primary light source included in the external control arrangement.

The probe further comprises a temperature sensor 2, preferably a thermocouple, for providing temperature data, and an electrical communication connection for transferring said temperature data to an external control arrangement.

The probe further comprises an acoustic receiver 3 for providing acoustic absorption data, and an electrical communication connection for transferring the absorption data to an external control arrangement.

Preferably, the acoustic receiver 3 is hydrophone, located behind the transmitter, i.e. in the central part of the housing. The hydrophone is arranged for receiving acoustical signals, which is used for calculating absorption data. The hydrophone may be directive. Energy absorption data may be provided by a processing device in the external control arrangement, based on hydrophone data. The processing is performed by a calculation process which include pressure difference data between the hydrophone(s) and transmitter and signal characteristics as its major input parameters. Scanline processors may be added in the processing device for tissue depth analysis.

The probe further comprises a locking arrangement, in particular a flexible jacket 8, arranged for locking the probe in a fixed position between or within organs. The flexible jacket 8 is arranged at the periphery of the probe, for improving the mechanical and acoustical connection between the probe and the cavity by supplying liquid into the jacket, thus pressurizing the jacket 8a.

Another purpose of the flexible jacket 8a is to increase the acoustic impedance. In the preferred embodiment, the flexible jacket comprises a liquid filled, ring of an expandable, flexible material which may be pressurized with liquid in order to increase the outer boundary or diameter of the probe. An accompanying pressure gauge 8b is preferably integrated as a feedback to avoid overload on internal organs.

The fluid is preferably distilled (degassed) water. The purpose of the fluid injection is to obtain maximum acoustic conductivity, the possibility for cleansing and as a medium for driving a locking means between the probe and the body tissue.

Figures 9, 10:
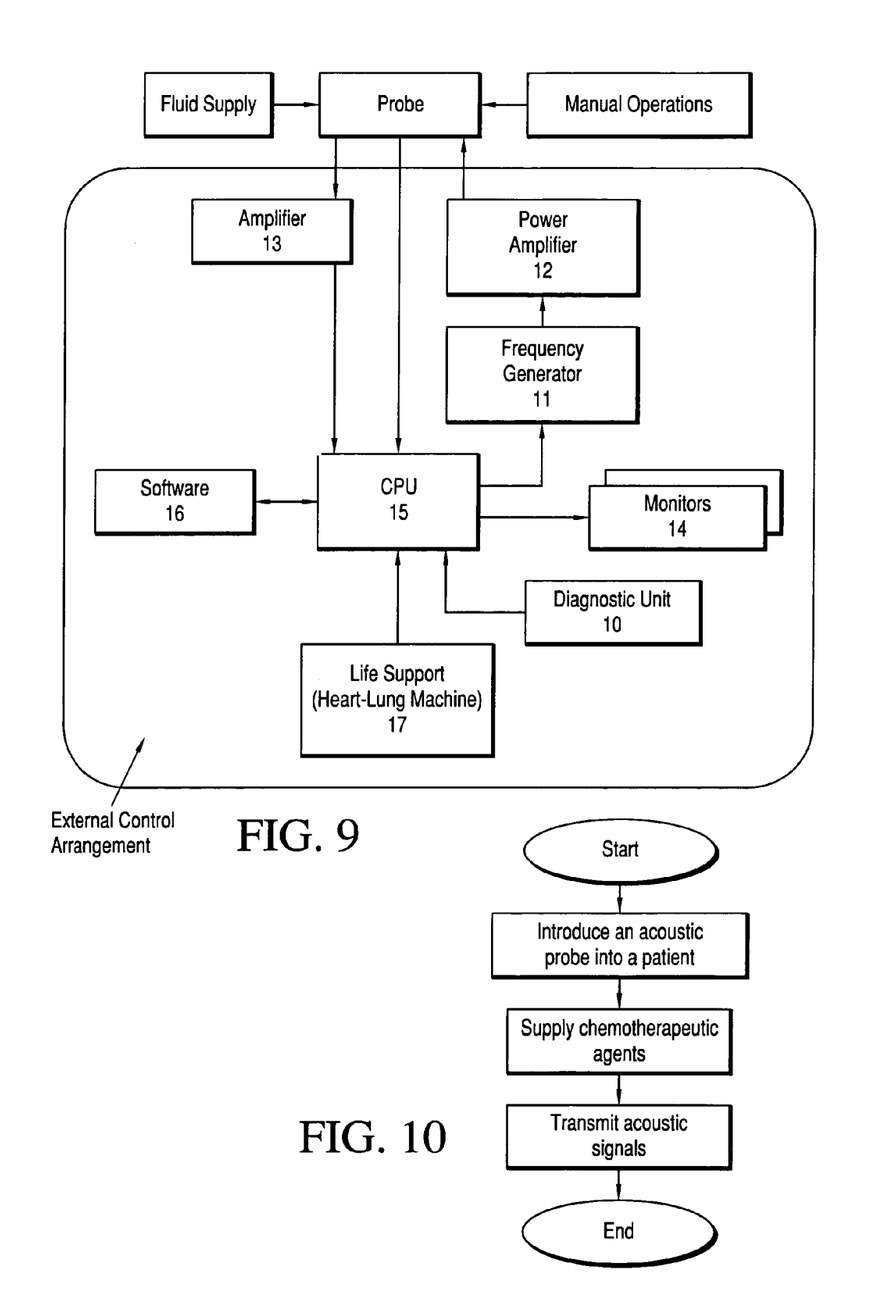
FIG. 9 is a schematic diagram illustrating a system according to the invention.
FIG. 10 is a flow chart illustrating a method according to the invention.

The flow is prepositioned and controlled from the CPU 15, and supplied to the probe through the flexible cord by a separate supply line, from an external storage and pressure facility, which is not detailed on FIG. 9.

The probe is further fitted with a connector/dismantling arrangement 9 which allows for the changing of probe heads with different directive orientations of the transmitter, different sizes of the probe head etc. The connector fits the various supply channels and electrical/optical cables between the housing 102 and the instrument body 106.

The probe may further comprise a longitudinal and/or bended instrument channel 6 for the application of tools and additional apparatuses to cut, burn, inject, provide additional cleansing (fluid), suction of fluid or debris, remove or manipulate tissue by any other means. The instrument channel 6 also allows for locally administered chemotherapeutic substances.

With reference to FIG. 9, a system for treating cancerous tissue is illustrated. The system comprises a probe according to the invention as described above, an external control arrangement operatively connected to the probe, and an external fluid (i.e., liquid) supply connected to the probe via a liquid connection line. Although not illustrated in FIG. 9, all connections to the probe are preferably fed through the flexible cord 1 illustrated in FIG. 7.

Figure 8:
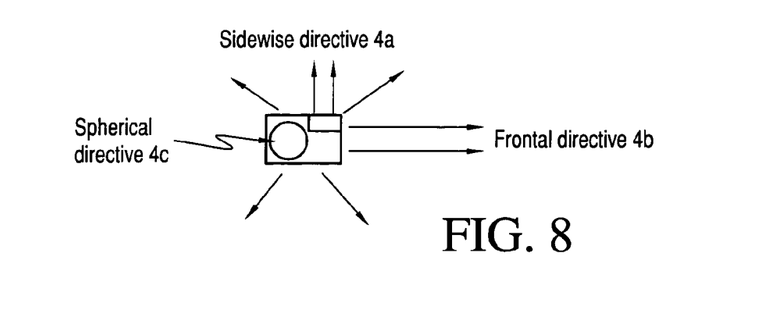
FIG. 8 is a schematic diagram illustrating various transmitter alternatives.

The external control arrangement comprises a standard diagnostic device 10, a frequency generator 11, a power amplifier 12, a preamplifier 13, monitors 14, a central processing unit CPU 15 and a computer program 16 for controlling the CPU 15. With reference to FIGS. 8a and 8b, electrical cables connecting the power amplifier 12 and the transmitter 4, the hydrophone 3 and the CPU 15, cables connecting the camera 8 and the CPU 15 and monitors 14 are provided. Electric cable from CPU 15 to a miniaturized fluid valve distributing fluid flow from the external fluid supply and pressure facility (not shown) for both acoustic contact 7a, cleansing 7b and locking 8 is provided. Feedback data from the pressure gage (not illustrated), the thermocouple 2 to the CPU 15 and input data (light level, fluid pressure, signal data etc.) are provided and displayed on the monitor(s) 14.

Chemotherapeutic agents may be provided locally through the instrument channel 6 or at a distant location within the body. In these cases, chemotherapeutic flow data are prepositioned and controlled by the CPU 15 and displayed 14.

The diagnostic unit can be of a standard ultrasound type, or based on x-ray, MR, PET or any other adequate technique. The aim is overall viewing, but to measure and control the distance from the tumour, cancerous tissue or organ to the transmitter, to avoid placing the tissue in question at a pressure minimum point, is of paramount importance.

The frequency generator 11 and power amplifier 12 are arranged to provide both frequencies and relevant intensities to the transmitter. A preamplifier 13 is connected to the hydrophone 3. Monitors 14 or scopes for viewing the vicinity of the probe, transmitted and received signals are provided. A CPU 15 and accompanying software 16 for guidance and control of the various components of the system is provided. Key elements in this respect are emitted intensity of the acoustic signal, type (continuous, pulsed etc.) and frequency of the signal, controlling the duration of exposure, analysis of receiving signals, control of the fluid flow and cytostatica. The actual guidance and control is governed by the computer program, in conjunction with the various settings. A portion of the computer program in combination with the received signal from the hydrophone 3, with or without the use of scanline processors, may analyse the intensity and/or the energy levels at the location of interest (tumour site) based upon provided coordinates, as a supplement or the replacement of a diagnostic unit.

The apparatus or probe and subsequent system may be integrated with heart-lung machines, respirators or any other life support or life sustaining system 17 if the heart/lung functions are suspended.

FIG. 10 is a flow chart illustrating a method for treating cancerous tissue according to the invention.

As shown in FIG. 10, the method comprises the steps of introducing an acoustic probe into a natural or surgically created cavity in the patient, in close proximity to a tissue area which includes cancerous cells, and transmitting an acoustic signal from the acoustic probe, said signal having characteristics which causes damage of said cancerous cells.

As explained above with reference to the probe illustrated in FIG. 7, the characteristics may include a natural resonance frequency of said cancerous cells, an apoptosis frequency of said cancerous cells, a necrosis frequency of said cancerous cells, or a decapsulating frequency releasing a cytostatic substance from micelles or therapeutic molecules, said frequency being in the range of 1 kHz to 1 MHz.

Figure 11A:
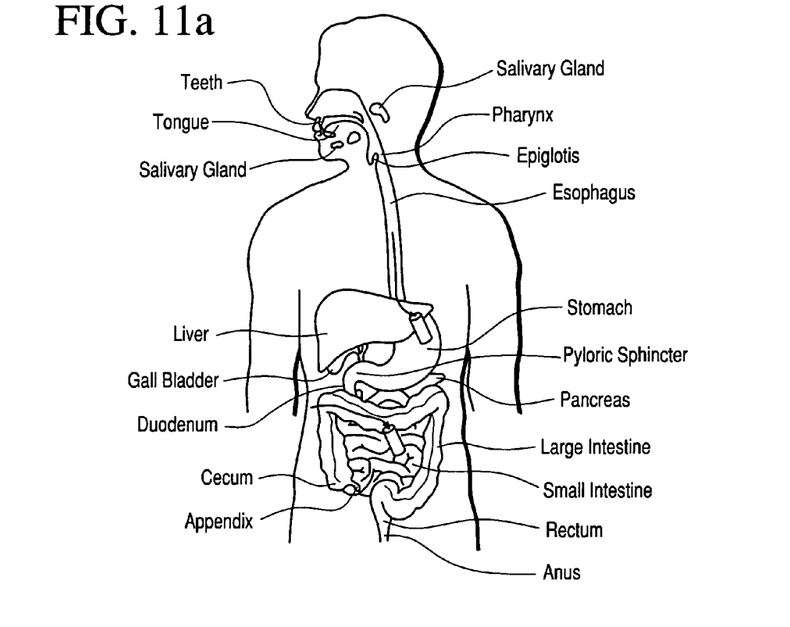
FIG. 11a–c illustrates various applications of a probe according to the invention.
Figure 11B:
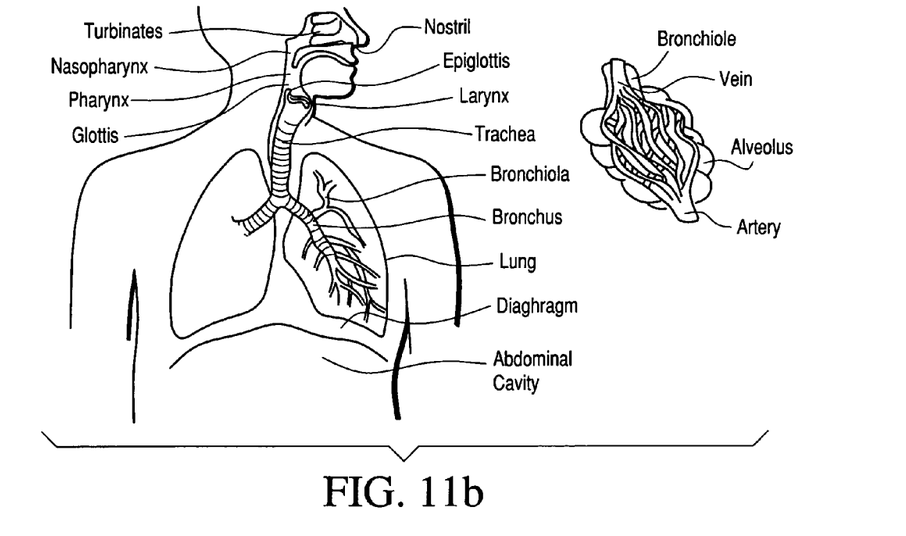
Figure 11C:
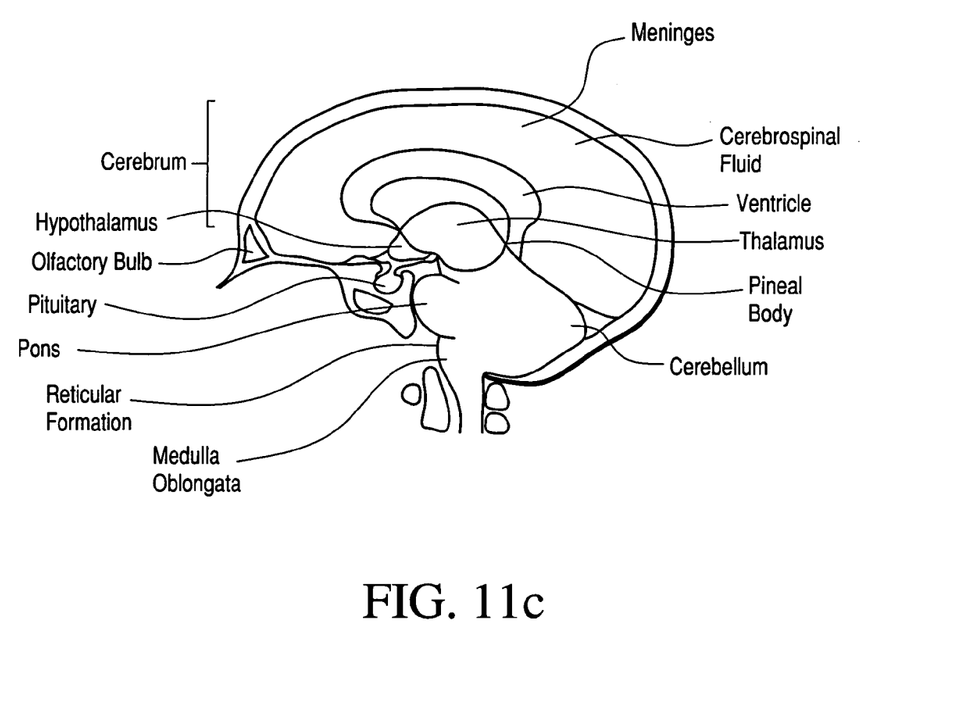

As further illustrated in FIG. 11, the method advantageously further comprises the step of supplying encapsulated chemotherapeutical agents within micelles to the patient. Although this additional supplying step has been illustrated to be performed subsequent to the transmitting step, it should be realized by the skilled person that the step of supplying a chemotherapeutical agent may as well be performed prior to the probe introducing step, or between the probe introducing step and the transmitting step, or even concurrently with either of the probe introducing step or the transmitting step.

The method advantageously further comprises the step of supplying a liquid from a liquid connection from an external liquid supply through a liquid connection line and further through at least one orifice in the probe, in order to provide an acoustic medium between the probe and the tissue. In a particular embodiment, the above mentioned chemotherapeutical agent is supplied by separate means, provided through the instrument channel of the probe and system.

The acoustic signal is preferably transmitted by a forward directive, sidewise directive or spherical directive transmitter included in the acoustic probe, said transmitter being supplied with an electrical signal from an external control arrangement by an electrical communication connection.

The method advantageously further comprises the step of providing image data by means of an optical viewing device included in the acoustic probe, said image data being transferred to an external control arrangement by an optical or electrical communication connection.

The method advantageously further comprises the step of providing temperature data by means of a temperature sensor included in the acoustic probe, said temperature data being transferred to an external control arrangement by an electrical communication connection.

The method advantageously further comprises the step of providing acoustic absorption data by means of an acoustic receiver included in the probe, said absorption data being transferred to an external control arrangement by an electrical communication connection.

The method advantageously further comprises the step of improving the mechanical and acoustical connection between the probe and the cavity, by supplying liquid into a flexible jacket at the periphery of the probe.

FIGS. 11a–c illustrates various applications of a probe and a method according to the invention. As illustrated, many alternatives exist for in vivo use of an acoustic transmitter probe for treating cancer, including gastro applications (FIG. 11a), chest applications (FIG. 11b) and head/neck applications (FIG. 11c).

The probe according to the invention can be inserted into the mouth, esophagus, stomach, the trachea or through the chest wall and into the chest cavity or abdominal wall. The organ or the surrounding body cavity may be partly or totally filled with liquid by separate arrangement. The probe may be inserted into all of the body orifices.

As a corollary of the description in FIG. 11b, a patient with e.g. a diagnosed lung cancer may be anesthesiased and connected to a heart-lung machine. The trachea is subsequently filled with fluid and the probe is inserted into or through the trachea. Encapsulated cytostatica is locally released into the lung tissue, through arrangements administered by the instrument channel of the probe, or by built-in (frontal or sidewise) drug injection means of the probe. Acoustics is applied through the probe for a defined duration. The trachea, lung or chest cavity is drained of fluid by means administered through the instrument channel and the probe is removed. Ordinary life functions are restored and the heart-lung machine is disconnected. The procedure may be repeated.

The invention has thus been described in detail by way of an example, with some alternatives indicated. A person skilled in the art will, however, realize that numerous variations and alternatives exist within the scope of the invention, as defined by the appended claims.

For instance, although the probe housing is illustrated with different dimensions of the distant and the proximal portions of the probe housing, it will be evident that the exterior and the shape of the probe may be modified according to the intended specific use.

In this respect the probe may be flexible in all directions (sidewise and/or longitudinal bendable) may be made out of flexible materials. The distal portion 106 and the shaft 104 may be flexibly jointed, the instrument channel may have a sidewise outlet. Drug delivery means may be built-in into the probe.

Likewise, as illustrated in FIG. 8, although the acoustic transmitter is primarily indicated as preferably being forward directive, it may alternatively be sidewise directive or spherical directive in relation to the intended specific use, and thus in accordance with the skilled person's choice.

It will be evident that the optical viewing device may comprise a lens and an optical communication line, rather than an electronic camera.

If necessary in relation to the specific use, the cord may be stiff rather than flexible.

The locking arrangement 8 may be an electromechanical device rather than the hydraulic jacket illustrated above.

The invention claimed is:

1. A non-invasive acoustic endoscopic probe for treating cancerous tissue, with a blunt end suitable for introduction into a natural cavity in a human or animal patient, in close proximity to a tissue area which includes cancerous cells, said probe comprising a body portion and a detachable head portion, said head portion being connected to said body portion by means of a connector, said body portion comprising a first electrical conductor and a first supply channel portion and said head portion comprising a second electrical conductor, a second supply channel portion, and an acoustic transmitter arranged for transmitting an acoustic signal having characteristics which cause damage of said cancerous cells, said connector connecting said first and second electrical conductors and said first and second supply channel portions.

2. Probe according to claim 1, wherein said characteristics are selected from a group consisting of a decapsulating frequency releasing a cytostatic substance from micelles or therapeutic molecules so as to cause said damage of said cancerous cells, and an interacting frequency working in synergy with a therapeutic substance so as to cause said damage of said cancerous cells.

3. Probe according to claim 2, further comprising at least one orifice for supplying a liquid from the probe, in order to provide an acoustic medium between the probe and the tissue or to provide cleansing, and a liquid connection line for supplying said orifice with said liquid from an external liquid supply.

4. Probe according to claim 3, wherein a chemotherapeutical agent is supplied through or from the probe.

5. Probe according to claim 3, further comprising a flexible jacket at the periphery of the probe, for improving the mechanical and acoustical connection between the probe and the cavity by supplying liquid into the jacket, wherein said liquid supplied to the flexible jacket is supplied by said liquid connection line.

6. Probe according to claim 2, wherein said acoustic transmitter is forward directive, sidewise directive or spherical directive, said probe further comprising an electrical communication connection for supplying said transmitter with an electrical signal from an external control arrangement.

7. Probe according to claim 2, further comprising an optical viewing device for providing image data, and an optical or electrical communication connection for transferring said image data to an external control arrangement.

8. Probe according to claim 2, further comprising a temperature sensor for providing temperature data, and an electrical communication connection for transferring said temperature data to an external control arrangement.

9. Probe according to claim 2, further comprising an acoustic receiver for providing acoustic absorption data, and an electrical communication connection for transferring the absorption data to an external control arrangement.

10. Probe according to claim 2, further comprising a flexible jacket at the periphery of the probe, for improving the mechanical and acoustical connection between the probe and the cavity by supplying liquid into the jacket.

11. Probe according to claim 1, wherein said acoustic signal has a frequency in the range of 1 kHz to 100 kHz.

12. Probe according to claim 1, wherein said acoustic signal has a frequency in the range of 1 kHz to 1 MHz.

13. Method of treating cancerous tissue, comprising the steps of non-invasively introducing an acoustic endoscopic probe having a blunt end into a natural cavity in the patient, in close proximity to a tissue area which includes cancerous cells, and transmitting an acoustic signal from the acoustic probe, said signal having characteristics which causes damage of said cancerous cells wherein said probe comprises a body portion and a detachable head portion, said head portion being connected to said body portion by means of a connector, said body portion comprising a first electrical conductor and a first supply channel portion and said head portion comprising a second electrical conductor and a second supply channel portion, said connector connecting said first and second electrical conductors and said first and second supply channel portions.

14. Method according to claim 13, wherein said characteristics are selected from a group consisting of a decapsulating frequency releasing a cytostatic substance from micelles or therapeutic molecules so as to cause said damage of said cancerous cells, and an interacting frequency working in synergy with a therapeutic substance so as to cause said damage to said cancerous cells.

15. Method according to claim 14, further comprising the step of supplying chemotherapeutical agent to the patient.

16. Method according to claim 14, further comprising the step of supplying a liquid from an external liquid supply through a liquid connection line and further through at least one orifice in the probe, in order to provide an acoustic medium between the probe and the tissue and/or cleansing.

17. Method according to claim 16, wherein a chemotherapeutical agent is supplied through or from the probe.

18. Method according to claim 14, wherein said acoustic signal is transmitted by a forward directive, sidewise directive or spherical directive transmitter included in the acoustic probe, said transmitter being supplied with an electrical signal from an external control arrangement by an electrical communication connection.

19. Method according to claim 14, further comprising the step of providing image data by means of an optical viewing device included in the acoustic probe, said image data being transferred to an external control arrangement by an optical or electrical communication connection.

20. Method according to claim 14, further comprising the step of providing temperature data by means of a temperature sensor included in the acoustic probe, said temperature data being transferred to an external control arrangement by an electrical communication connection.

21. Method according to claim 14, further comprising the step of providing acoustic absorption data by means of an acoustic receiver included in the probe, said absorption data being transferred to an external control arrangement by an electrical communication connection.

22. Method according to claim 13, further comprising the step of improving the mechanical and acoustical connection between the probe and the cavity, by supplying liquid into a flexible jacket at the periphery of the probe.

23. Probe according to claim 13, wherein said acoustic signal has a frequency in the range of 1 kHz to 100 kHz.

24. Probe according to claim 11, wherein said acoustic signal has a frequency in the range of 1 kHz to 1 MHz.

25. System for treating cancerous tissue, comprising a non-invasive acoustic endoscopic probe for treating cancerous tissue, having a blunt end suitable for introduction into a natural cavity in the patient, in close proximity to a tissue area which includes cancerous cells, and an external control arrangement operatively connected to said probe, wherein said probe comprises a body portion and a detachable head portion, said head portion being connected to said body portion by means of a connector, said body portion comprising a first electrical conductor and a first supply channel portion and said head portion comprising a second electrical conductor, a second supply channel portion, and an acoustic transmitter arranged for transmitting an acoustic signal having characteristics which causes damage of said cancerous cells, said connector connecting said first and second electrical conductors and said first and second supply channel portions.

26. System according to claim 25, wherein said characteristics are selected from a group consisting of a decapsulating frequency releasing a cytostatic substance from micelles or therapeutic molecules so as to cause said damage of said cancerous cells, and an interacting frequency working in synergy with a therapeutic substance so as to cause said damage of said cancerous cells.

27. System according to claim 26, wherein the probe further comprises at least one orifice for supplying a liquid from the probe, in order to provide an acoustic medium between the probe and the tissue or to provide cleansing, said system further comprising an external liquid supply, and a liquid connection line for supplying said orifice with said liquid from said external liquid supply.

28. System according to claim 27, wherein a chemotherapeutical agent is supplied through or from the probe.

29. System according to claim 26, wherein said acoustic transmitter is forward directive, sidewise directive or spherical directive, said system further comprising an electrical communication connection for supplying said transmitter with an electrical signal from the external control arrangement.

30. System according to claim 26, wherein the probe further comprises an optical viewing device for providing image data, said system further comprising an optical or electrical communication connection for transferring said image data to the external control arrangement.

31. System according to claim 26, wherein the probe further comprises a temperature sensor for providing temperature data, said system further comprising an electrical communication connection for transferring said temperature data to the external control arrangement.

32. System according to claim 26, wherein the probe further comprises an acoustic receiver for providing acoustic absorption data, said system further comprising an electrical communication connection for transferring said absorption data to the external control arrangement.

33. System according to claim 26, wherein the probe further comprises a flexible jacket at the periphery of the probe, for improving the mechanical and acoustical connection between the probe and the cavity by supplying liquid into the jacket.

34. System according to claim 26, wherein said external control arrangement comprises a frequency generator, a diagnostic device, a power amplifier, a preamplifier, a monitor, a central processing unit and a computer program for controlling the CPU.

35. System according to claim 26, wherein said external control arrangement comprises a life support system.

36. Probe according to claim 25, wherein said acoustic signal has a frequency in the range of 1 kHz to 100 kHz.

37. Probe according to claim 21, wherein said acoustic signal has a frequency in the range of 1 kHz to 1 MHz.

38. Apparatus for treating cancerous tissue, the apparatus comprising a non-invasive endoscopic acoustic probe for introduction into a natural cavity in a human or animal patient, in close proximity to a tissue area which includes cancerous cells, an external control arrangement, and a flexible cord connecting between the probe and the external control arrangement, wherein the probe comprises a body portion and a detachable head portion, said head portion being connected to said body portion by means of a connector, said body portion comprising a first electrical conductor and a first supply channel portion and said head portion comprising a second electrical conductor, a second supply channel portion, a front face, an optical viewing device provided at the front face, and an acoustic transmitter arranged for transmitting an acoustic signal having characteristics which cause damage to said cancerous cells, said connector connecting said first and second electrical conductors and said first and second supply channel portions; wherein said optical viewing device and said acoustic transmitter are connected to said external control arrangement via said flexible cord.

39. Apparatus according to claim 38, further comprising a shaft protruding from the proximal end of the instrument body and connecting the instrument body to the flexible cord, said shaft having a diameter smaller than that of the instrument body.

40. Probe according to claim 38, wherein said acoustic signal has a frequency in the range of 1 kHz to 100 kHz.

41. Probe according to claim 36, wherein said acoustic signal has a frequency in the range of 1 kHz to 1 MHz.

\* \* \* \* \*